United States Patent
Means et al.

[11] Patent Number: 6,104,032
[45] Date of Patent: *Aug. 15, 2000

[54] FILTER INSPECTION SYSTEM

[76] Inventors: Orville D. Means, 12555 Kirkham Rd. Ste. 200, Poway, Calif. 92064; Robert W. LeClair, 2243 Bent Tree Pl., Escondido, Calif. 92026; David S. Furuno, 15791 Caminito Cercado, San Diego, Calif. 92128

[ * ] Notice: This patent is subject to a terminal disclaimer.

[21] Appl. No.: 08/239,732

[22] Filed: May 9, 1994

Related U.S. Application Data

[63] Continuation-in-part of application No. 07/959,700, Oct. 13, 1992, Pat. No. 5,311,023.

[51] Int. Cl.[7] .......................... G01N 21/88; G01N 21/894
[52] U.S. Cl. ........................................ 250/341.7; 356/237
[58] Field of Search .............................. 250/341.7, 359.1, 250/360.1, 562, 563, 358.1, 347, 224, 236, 559.42; 356/426, 237

[56] References Cited

U.S. PATENT DOCUMENTS

| | | | |
|---|---|---|---|
| 3,324,633 | 6/1967 | Revell | 250/562 |
| 3,509,352 | 4/1970 | Nash et al. | 250/562 |
| 3,800,157 | 3/1974 | Nichols | 250/353 |
| 4,247,204 | 1/1981 | Merlen et al. | 356/237 |
| 4,279,508 | 7/1981 | Everroad | 356/237 |
| 4,302,105 | 11/1981 | Sick | 356/237 |
| 4,323,311 | 4/1982 | West et al. | 356/431 |
| 5,311,023 | 5/1994 | Means, Jr. et al. | 250/349 |

FOREIGN PATENT DOCUMENTS

| 57938 | 5/1981 | Japan | 356/426 |
|---|---|---|---|

*Primary Examiner*—Constantine Hannaher
*Attorney, Agent, or Firm*—Baker & Maxham

[57] ABSTRACT

A filter inspection system for inspecting filters comprising a support frame for supporting a substantially tubular filter having inner and outer surfaces for rotation about its axis, a source of EMR for directing radiation along one of the inner and outer surfaces of a filter, an EMR sensing unit mounted adjacent to the other of the surfaces for sensing EMR passing through the filter and generating a signal, and an indicator responsive to the signal for indicating the existence of and the location of passage of EMR through the filter.

15 Claims, 4 Drawing Sheets

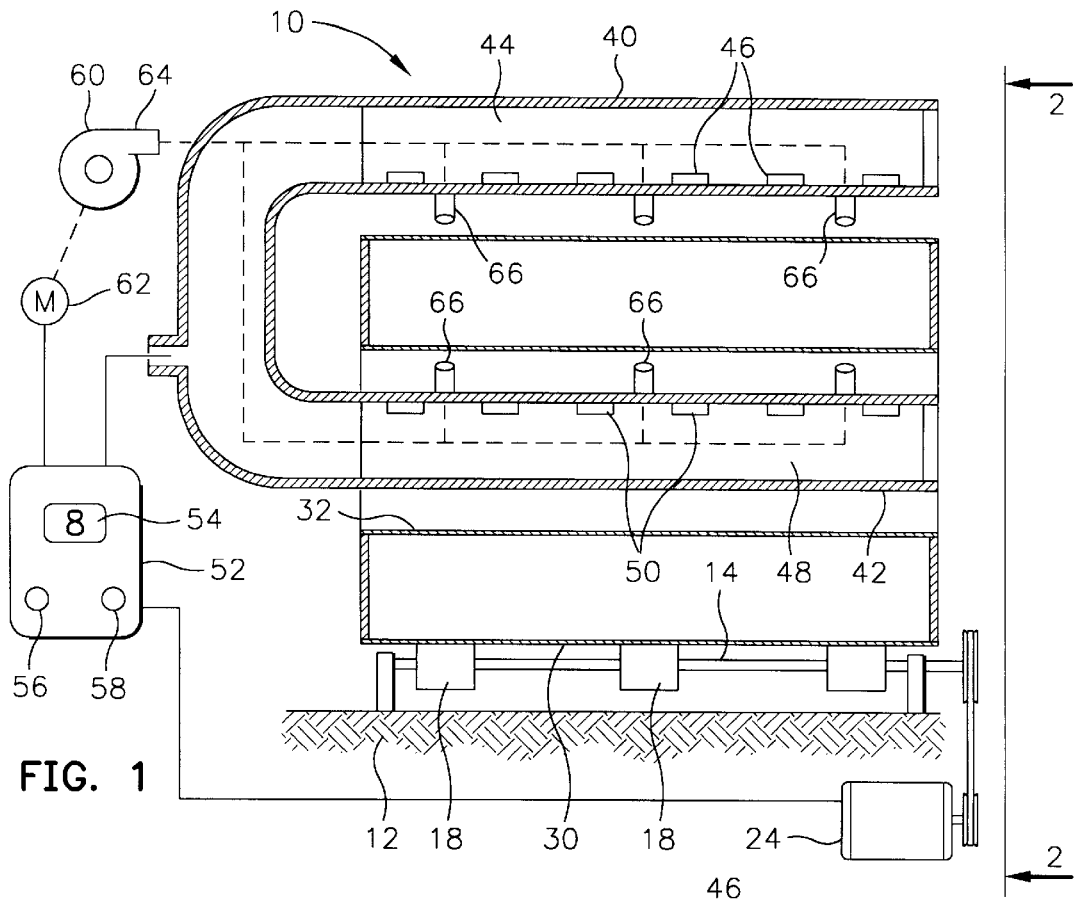
FIG. 1
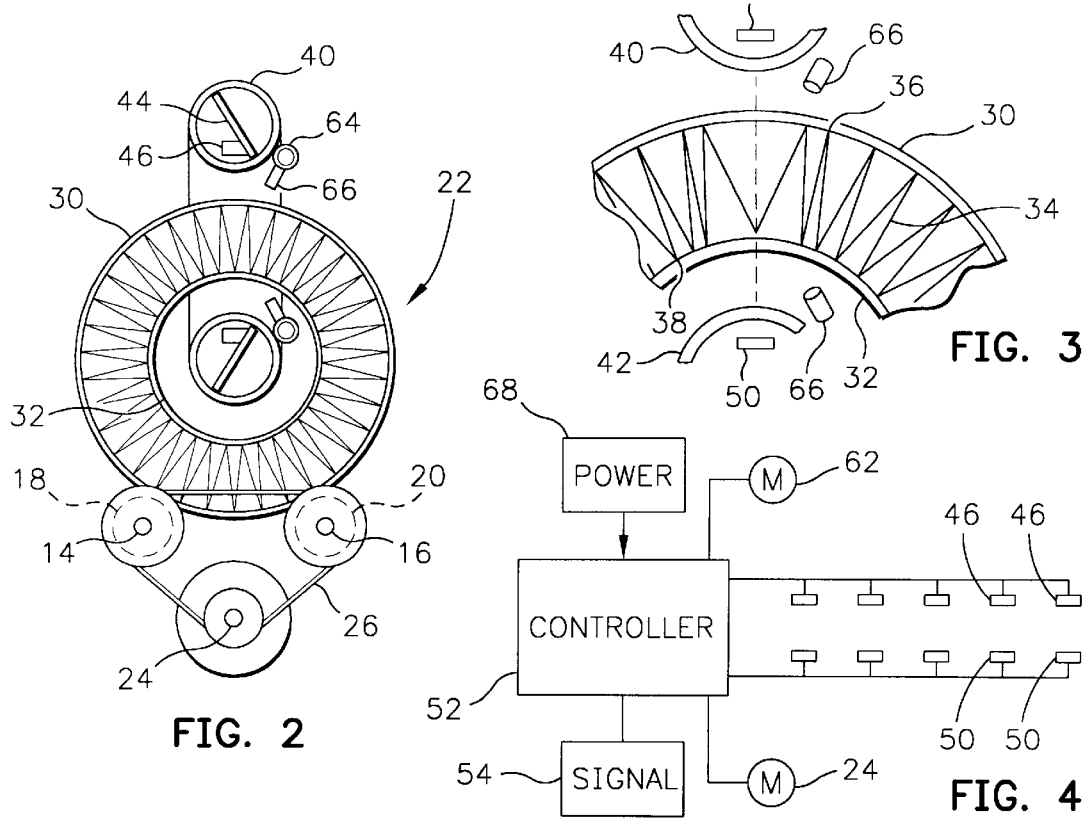
FIG. 2
FIG. 3
FIG. 4

_6,104,032_

FILTER INSPECTION SYSTEM

REFERENCE TO RELATED APPLICATION

This is a continuation-in-part of application Ser. No. 07/959,700 filed Oct. 13, 1992, entitled "FILTER INSPECTION APPARATUS", now U.S. Pat. No. 5,311,023.

BACKGROUND OF THE INVENTION

The present invention relates to inspection systems and pertains particularly to an improved filter inspection system.

Internal combustion engines, gas turbines, and other air breathing machines are subject to damage from dirt, grit and the like that gets into the intake combustion air that they breathe. Therefore, they must have source of intake air that is clean and free of dirt, grit and debris. Most such machines utilize filters to filter dirt, grit and other debris from the air drawn into the machinery. Most such filters currently in use are of a large cylindrical tubular configuration, with some being tapered somewhat.

The filters are typically formed of inner and outer wire mesh or perforated metal screens, with a corrugated paper filter there between. The filter paper is formed to have a large surface area to allow the passage of air but to trap fine dirt and grit particles. The filter paper is typically formed with a fan or corrugated fold in order to provide a large surface area for the passage of large volumes of air and entrapment of dirt and grit particles. These filters typically cost between thirty-five and eighty-five dollars each. Therefore, filter replacement can become quite expensive when operating in dirty and dusty environments, such as mining, road building and other earth working environments.

It has been customary in the past to clean the filters a limited number of times by washing them in a solvent or the like. The filters can be typically cleaned in this manner two to three times before they must be discarded.

A cleaning system has been recently developed as set forth in U.S. Pat. No. 5,143,529 granted to co-inventor Means herein that further extends the life of filters. That system provides a dry process for cleaning filters that enables them to be cleaned multiple times with no perceptible damage. However, filters do develop small holes from various sources, including cleaning and reuse that render them unusable. These small holes can let sufficient dirt or grit through to severely damage an engine. They usually develop in the crease or fold of the filter paper and are difficult to detect by traditional visual inspection.

Visual inspection of the filters by means of a visible source of light, such as disclosed in Everrod U.S. Pat. No. 4,279,508 is the most common form. However, such visual inspection is subject to the good eyesight, skill and concentration of the inspector. It is also subject to human error and judgment, even with light amplifiers or intensifiers as disclosed in Everrod.

In the aforementioned parent application, there is disclosed improved apparatus using infrared radiation (IR) light sources and IR detectors. However, these also have drawbacks and are not entirely satisfactory.

It is desirable that improved apparatus and methods be available to reliably inspect filters.

SUMMARY OF THE INVENTION

It is the primary object of the present invention to provide an improved filter inspection apparatus.

In accordance with a primary aspect of the present invention, a filter inspection apparatus for inspecting generally cylindrical filters comprises means for supporting a filter, a source of electromagnetic radiation (EMR) for directing against one surface of the filter, air nozzle means mounted for movement with said EMR source along the surface of a filter for spreading the folds of the filter, and EMR sensing means on the opposite side of the filter for detecting the passage of EMR therethrough.

BRIEF DESCRIPTION OF THE PREFERRED EMBODIMENTS

The above and other objects and advantages of the present invention will become apparent from the following description when read in conjunction with the accompanying drawings wherein:

FIG. 1 is a side diagrammatic elevation view of a preferred embodiment of the invention;

FIG. 2 is a right side end view of the embodiment of FIG. 1;

FIG. 3 is an enlarged partial sectional view of a portion of FIG. 2;

FIG. 4 is a functional block diagram of the control system of the invention;

DETAILED DESCRIPTION OF THE PREFERRED EMBODIMENTS

Figure 5:
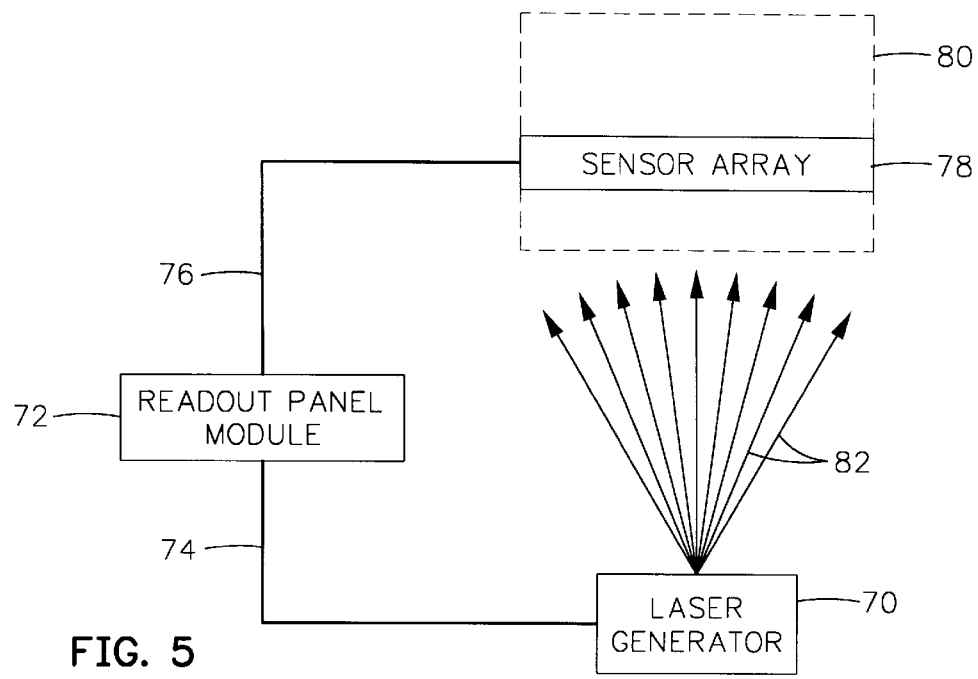
FIG. 5 is a schematic illustration of an alternate embodiment of the invention.

Referring to FIGS. 1 and 2 of the drawings, diagrammatic illustration of an exemplary embodiment of the invention is shown and designated generally by the numeral 10. The illustrated embodiment comprises a generally horizontally extending support frame structure of a somewhat generally rectangular construction.

The illustrated apparatus, designated generally by the numeral 10, comprises a suitable base frame 12 having suitable support or mounting means for a filter, such as a pair of spaced apart shafts 14 and 16, on which are mounted a plurality of rollers 18 and 20. At least some of these rollers are preferably keyed or fixed to the shaft to rotate therewith and cause rotation of a filter, designated generally at 22, when said filter is supported thereon. A suitable motor, such as an electrical motor 24, drives the shafts through a belt 26 and pulley 28.

The apparatus, as illustrated, is designed primarily to inspect larger tubular type air filters which are typically used in large trucks and earth moving equipment. Such filters are preferably cleaned for reuse and recycling in machines, such as disclosed in the aforementioned Means' patent which is incorporated herein by reference as though fully set forth. These filters are typically constructed of outer and inner wire mesh cylinders 30 and 32 between which is disposed a filter paper folded in an accordion or fan fold fashion, as illustrated in FIGS. 2 and 3. This folding provides a large surface area of panels between folds for trapping dust, grit and debris. The filter paper insert is folded to form and define outer folds 36 and inner folds 38 where holes typically occur. The present invention is designed to inspect filters and locate these holes with minimum error. Many times the holes can be patched by suitable doping compound, thereby enabling reuse and considerable savings in costs and expenses to a vehicle operator.

The apparatus comprises means for detecting holes in the filter by means of electro magnetic radiation (EMR), preferably in the form of coherent light or radiation directed against one surface of the filter, and means for detecting passage of the light through the filter on the other side of the filter surface. We have discovered that lasers have an advantage over traditional IR radiation sources for this application and for most conditions. The main characteristic of laser light is its coherence, although it is also usually more intense, more chromatic and collimated than light from other sources. Coherence is the property wherein corresponding points on the wave front are in phase. In the parent application the EMR was described as being preferably IR with the source being light emitting diodes (LED). An exemplary embodiment of the apparatus comprises support structure, which is the illustrated embodiment comprises a generally U-shaped transparent tube formed of a transparent plastic or glass or the like. It may also be of other materials with transparent windows and other configurations, where desired.

In the illustrated embodiment, the support member has an outer arm 40 for extending along an outer surface of a filter, and an inner arm 42 for extending into the bore of a filter. An electronic EMR transmission circuit is formed principally on a PC board 44, and disposed or mounted within the outer tube arm 40. This EMR transmission circuit includes a plurality of diodes 46 which may be IR or laser diodes mounted within the upper tube 40, and positioned to direct EMR against the outer surface of the filter. In the preferred form, the emitter diodes are laser diodes and are distributed continuously along the length of the tube, which is preferably long enough to accommodate the largest filter to be inspected.

An exemplary embodiment for IR contains two-hundred sixteen IR emitters for accommodating a twenty-four inch long filter. A laser source of this arrangement may require more laser emitters due to the nature of the light emitted. It is also possible to utilize a single emitter or small group of emitters mounted on a moveable arm to move along the axis of the filter. An alternate embodiment for a laser source of light shows another arrangement to be described.

An EMR receiver circuit is formed on a PC board 48 mounted within the tube 42, and containing a plurality of EMR receivers or sensors 50 disposed therealong, preferably grouped into two inch intervals, each containing seven. The transmitter and receiver circuits are preferably wired to a controller 52 (FIG. 4). The controller 52 may be simple switching controls, but preferably includes a CPU and suitable means for providing a signal, such as a digital readout 54 of the sensor which senses the transmission of EMR. It may also preferably include means to stop the drive instantaneous as EMR is sensed, so that a hole or opening in the filter may be readily located.

The receivers or group of receivers are preferably numerically identified in sequence, such as for example starting at one end, such as the outer end with one and numerically numbered up to the final number toward the left hand end of the apparatus as shown in FIG. 1. Thus, a sensor eight or group of sensors eight sensing the transmission of EMR will cause the controller to display the digit eight on the readout 54. The operator can then locate the hole at or near the number eight sensor or group of sensors. The controller 52 may include two or more switches 56 and 58 for power and for activation of the system generally. In the alternative, the system may be entirely manually controlled with switches for turning on and off the various circuits, and light indicators indicating the respective source of sensing EMR. Details of the transmitter and receiver circuits are disclosed in the parent application which is fully incorporated herein by reference as though fully set forth.

The apparatus is preferably provided with a source of pressurized air, which for example may be a blower or compressor 60 driven by a motor 62 for blowing air by way of a suitable conduit 64, and a plurality of ports or nozzles 66 onto the outer, inner or both surfaces of the filter. The apparatus is shown with a source of air blowing on both surfaces of the filter which causes the filter folds to separate, as shown in FIG. 3, to more clearly expose openings at either the outer or inner folds of the paper filter element to the source of light. The air will separate the fold panels as shown in FIG. 3 as the filter rotates, thus providing a greater expose of the edges of the filter unit to the EMR. This provides a more reliable chance that a tear or hole in the filter will be detected by the passage of EMR radiation therethrough.

The system may be powered by a suitable external power source 68 or by batteries, as illustrated in the system block diagram of FIG. 4. The air source may also be a blower or compressor incorporated in the apparatus or may be from an external source. For example, most automotive repair shops have large compressors with ample source of compressed air.

Referring to FIG. 5, there is diagrammatically illustrated an alternate embodiment of the invention utilizing a laser scan array. A laser scan generator 70 is connected to a control and readout panel module 72 by a suitable conductive cable 74. The control module is connected by a suitable cable 76 to a sensor array 78 which is illustrated as being inside a filter 80 under test. The sensor array is a suitable support containing an array of opto-electric sensors such as silicon solar cells, cadmium sulfide solar cells, photo transistors, photo darlington transistors, and pyroelectric detectors. The laser generator 70 may be of any suitable type gas, liquid, crystal or semiconductor that produces a suitable laser beam. The scan generator preferably produces a fan-like scanning pattern of one or more light beams 82 in a plane along the axis of the filter. This may be accomplished by a single continuous wave beam reflected by a rotating faceted mirror to create a moving beam along the surface of the filter.

Figure 6:
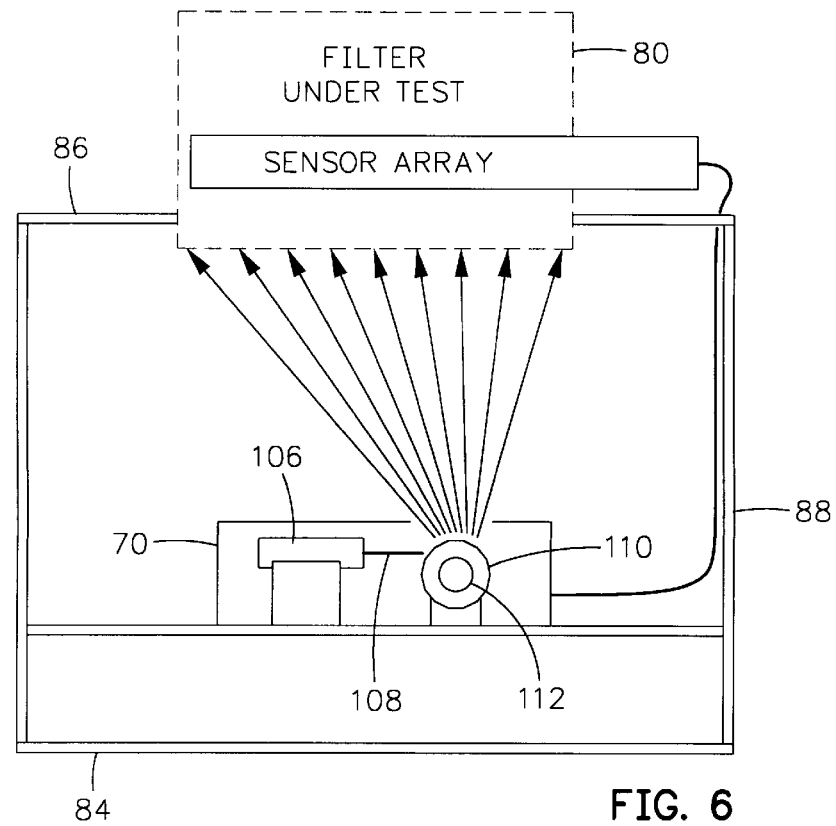
FIG. 6 is a side elevation view of the embodiment of FIG. 5.
Figure 7:
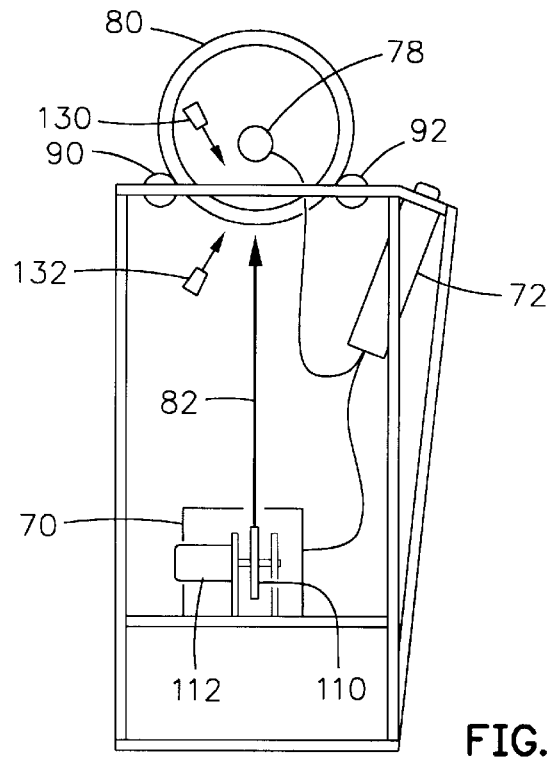
FIG. 7 is an end elevation view of the embodiment of FIG. 5.
Figure 8:
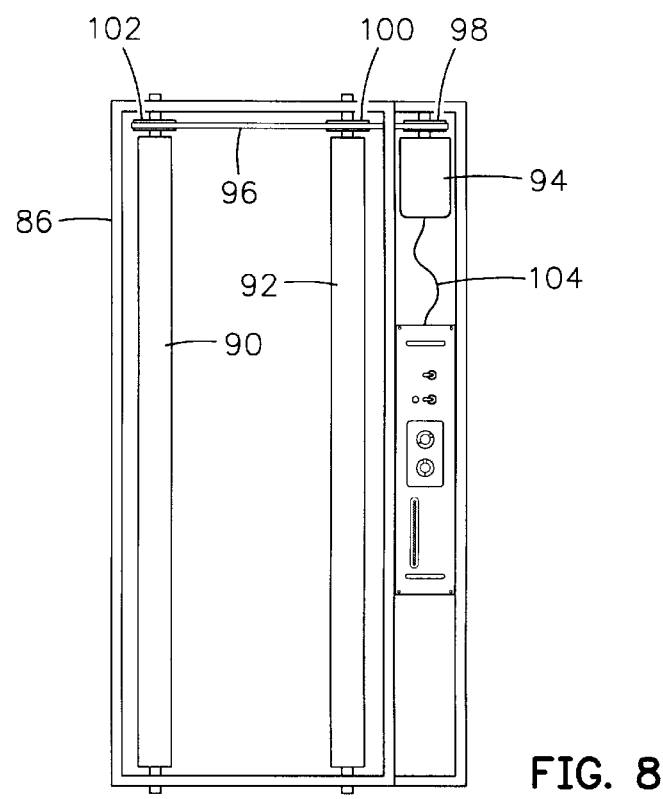
FIG. 8 is a top plan view of the embodiment of FIG. 5.

Referring to FIGS. 6, 7 and 8, there is illustrated an exemplary embodiment of a structure embodying the components of FIG. 5 in an inspection apparatus. As illustrated, the overall apparatus comprises a generally box-like frame or housing in which the basic components as seen in FIG. 5 are mounted. As illustrated, the housing includes a generally rectangular base-frame 84 and a similar vertically spaced top or upper frame 86. The upper and lower frames are secured together by four vertical frame members 88. A pair of spaced apart rollers 90 and 92 are mounted on the upper frame 86 for support and driving of a rotation of a filter as illustrated.

The support rollers are preferably rotatably mounted on top of the housing and extend horizontally and parallel along the major dimensional length of the housing. The rollers are driven by a suitable motor 94 through a belt 96 and pulleys 98, 100 and 102. The motor 94 is controlled via the control module by a conductive cable 104. The scan generator 70 is preferably placed in the bottom substantially center of the housing such that the scan ray therefrom extends directly upward and along the axis and lower surface of the filter 80 being tested. A sensor array is mounted within a tubular housing 78 and is positioned such that it extends into the center of the filter as illustrated in FIGS. 6 and 7 and preferably close to the inner surface thereof. Thus, rays generated by the laser scanner 70 which pass through the filter are picked up or sensed by the sensor array which transmits a signal to a control readout unit on the control panel of the control module. The control module is preferably mounted to the side of the housing (FIG. 7) with a control face panel directed upward and providing information for the operator as illustrated in FIG. 10.

Referring to FIGS. 6 and 7 the laser scan generator comprises a housing in which is mounted a laser generator 106 which generates and directs a light beam 108 onto a rotating faceted mirror wheel 110 driven by a motor 112. The light may be any suitable wave length such as visible, infrared or ultraviolet. Non-visible is preferred because it can be operated without the need for enclosure and would have less interference. The source of light can be any continuous wave or pulsed laser including gas, liquid, crystal and semiconductor or solid state.

Figure 9:
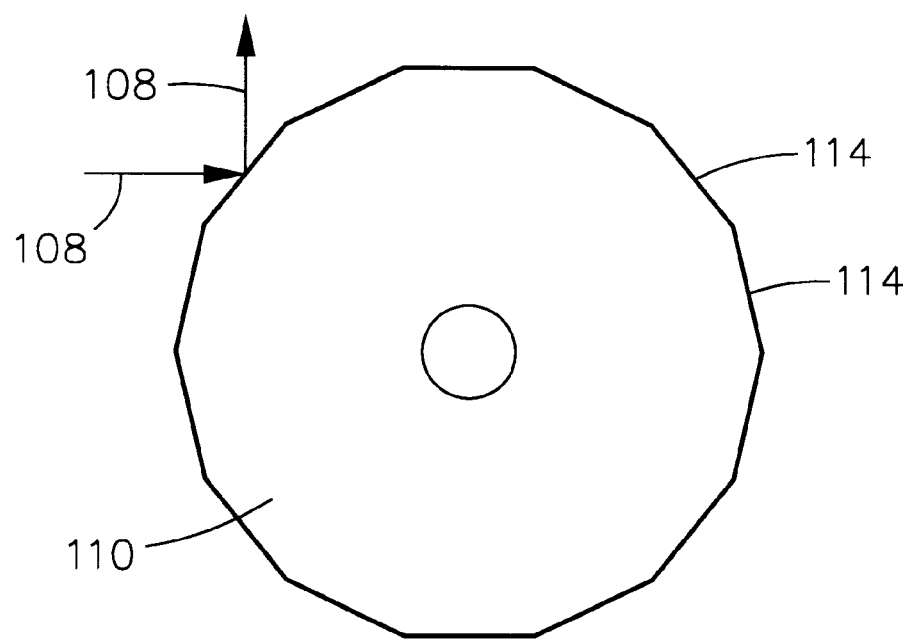
FIG. 9 is an enlarged detail view of the rotating mirror which sweeps the light beam.

The mirror wheel 110, as shown in FIG. 9, has a plurality of mirror faces 114 around the periphery thereof. As the wheel rotates, the beam 108 is reflected at a constantly changing angle and sweeps across the length of the filter. Each mirror segment 114 causes the reflected beam to sweep across the filter.

Figure 10:
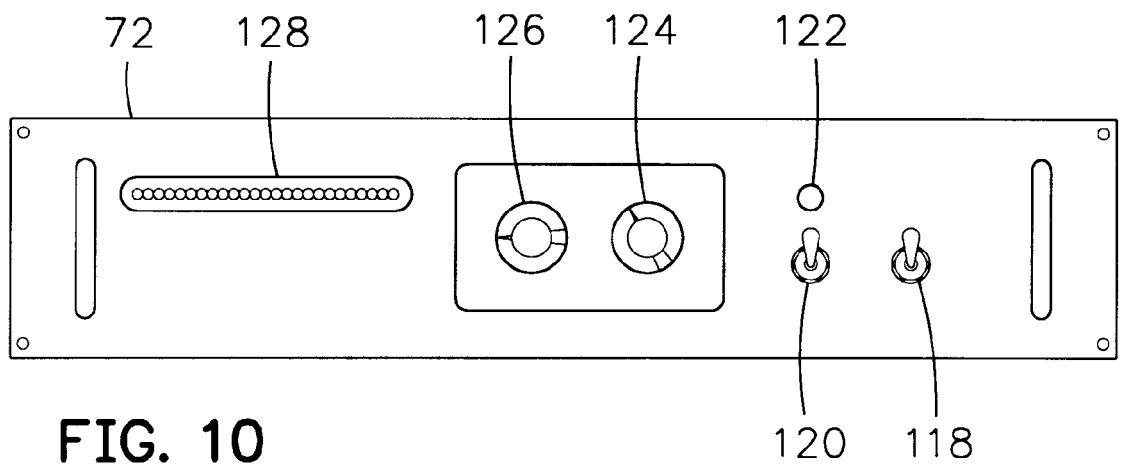
FIG. 10 is a front view of a control panel for the embodiment of FIG. 5.

A control panel 116 such as illustrated in FIG. 10 covers the face of the control module and includes an on-off switch 118, a reset button or switch 120 and a fail indicator 122. The fail indicator is a green light and is functional when the filter fails to turn red for example. However, it may be a light which merely illuminates upon the failure of a filter. The control module preferably has manual and automatic selection as a by selector switch 124 for selecting one or the other thereof. A sensitivity adjustment may also preferably be provided. The control module preferably contains a CPU as in the earlier embodiment (FIG. 1).

Means to indicate the location of the defect or hole in the filter is provided in the form of an elongated indicator array of LEDs 128 positioned along a length of the control panel, as indicated. The LEDs are responsive to the sensor array to illuminate upon the sensing of a hole in the filter with a particular LED indicating the position along the length of the filter where the hole occurs. This embodiment also preferably has air jets 130 and 132 as in the prior embodiment to separate folds of the filter when needed.

Thus, in operation as filters are cleaned by a suitable process, such as in the aforementioned patent, the cleaned filter is inspected by mounting in a apparatus as above described. The filter is supported on rollers 18 and 20, and the apparatus activated so as to rotate the filter as the laser or IR transmission circuit is activated. If IR or laser radiation passes through the filter and is detected by the detection circuit, a signal is indicated to the operator who then immediately stops the rotation of the filter and locates the hole visually. He may then, as previously stated, either repair the hole in the filter or discard the filter.

While the present invention was developed for inspecting generally tubular, including somewhat conical filters, it is apparent that with minor modifications I can also inspect non-tubular filters. For example, certain filters exist which have a generally V-through configuration. These, and others having either a curved (i.e. semicircular) or flat planar configuration can be inspected by slight modifications to the filter support and limiting the rotation of the filter clamp or support to an oscillation. The filters can be mounted in the machine and moved so that the sensing and transmitting heads move along the opposed faces thereof while inspecting the filter. It will also be apparent that the inspection apparatus can be incorporated into a cleaning device as disclosed in the aforementioned patent.

While we have illustrated and described our invention by means of specific embodiments, it should be understood that numerous changes and modifications may be made therein without departing from the spirit and scope of the invention as defined in the appended claims.

We claim:

1. A filter inspecting apparatus for inspecting generally tubular filters, comprising:

support frame;

mounting means mounted on said support frame for mounting a substantially tubular filter having inner and outer surfaces for rotation about its axis;

EMR generating means mounted on said support frame for generating and directing electromagnetic radiation;

a rotatable multifaceted mirror positioned for receiving electromagnetic radiation directly from said generating means and directing said electromagnetic radiation in a continuous sweep directly onto and along one of said inner and outer surface of the filter;

EMR sensing means mounted adjacent to the other of said inner and outer surfaces for sensing EMR passing through said filter and generating a signal responsive thereto;

indicator means responsive to said signal for indicating passage of EMR through the filter; and means for directing air against one of said surfaces of said filters for separating folds therein.

2. A filter inspecting apparatus according to claim 1 wherein said EMR generating means is a laser and said mirror is positioned for directing the EMR in a fan pattern along the outer surface and in a plane parallel to the axis of the filter.

3. A filter inspecting apparatus according to claim 1 wherein said EMR generating means is a laser and has a wave length outside the infrared light range.

4. A filter inspecting apparatus according to claim 1 wherein said EMR generating means is a semiconductor.

5. A filter inspecting apparatus according to claim 1 wherein said EMR sensing means comprises a plurality of laser light sensing elements mounted along the length of an elongated support member extending along the inner surface of the filter.

6. A filter inspecting apparatus according to claim 5 wherein said EMR sensing means comprises a plurality of EMR sensing elements grouped at intervals along the length of said support member.

7. A filter inspecting apparatus according to claim 5 wherein EMR generating means is a laser transmitter module disposed below said mounting means and includes said rotating faceted mirror directing the EMR at a constantly changing angle to the axis of the filter.

8. A filter inspecting apparatus according to claim 7 wherein said laser is a semiconductor laser.

9. A filter inspecting apparatus according to claim 1 wherein said EMR generating means is a laser; and said radiation is directed along the filter by a rotating mirror.

10. A filter inspecting apparatus according to claim 1 wherein said EMR generating means is a laser taken from the group consisting of gas, liquid, crystal and semiconductor.

11. A filter inspecting apparatus for inspecting tubular filters, comprising:

a support frame;

self-aligning mounting means including a pair of spaced apart parallel rollers mounted on said support frame, the rollers having outer cylindrical surfaces adapted for engaging the outer surface of and supporting a substantially tubular filter having inner and outer surfaces for rotation about its axis;

drive means for driving said rollers for rotating the filter;

a laser mounted for directing a beam of radiation;

a rotatable multifaceted mirror positioned for receipt of said beam of radiation directly from said laser and for directing said beam in a continuous sweep directly onto and along one of said inner and outer surface of the filter;

radiation sensing means mounted adjacent to the other of said inner and outer surfaces for sensing radiation passing through said filter and generating a signal responsive thereto;

indicator means responsive to said signal for indicating the existence and location of passage of radiation through said filter; and further comprising means for directing air against one or both of said surfaces of said filter for separating folds therein.

12. A filter inspecting apparatus according to claim 11 wherein said laser is mounted below said support frame for directing said beam of light along said outer surface of a filter;

sensing means adjacent said inner surface of the filter for sensing light passing therethrough; and a control panel having said indicator means mounted thereon, said indicator means indicating the location of light passing through the filter.

13. A filter inspecting apparatus according to claim 11 wherein said laser is taken from the group consisting of gas, liquid, crystal and semiconductor.

14. A filter inspecting apparatus comprising:

a support frame;

mounting means comprising a pair of spaced apart rollers on said support frame for supporting a substantially tubular filter having inner and outer surfaces for rotation about its axis;

means for rotating said rollers for rotating said filter;

a source of coherent light mounted intermediate the ends of said rollers;

a rotatable multifaceted minor positioned adjacent said source of light for receipt of a beam of said light directly from said source and for directing said beam in a continuous sweep directly onto and along one of said inner and outer surface of said filter;

coherent light sensing means mounted adjacent to the other of said inner and outer surfaces for sensing coherent light passing through said filter and generating a signal responsive thereto;

indicator means responsive to said signal for indicating passage of coherent light through said filter; and means for directing air against one of said surfaces of said filter.

15. A filter inspecting apparatus according to claim 14 wherein said source of coherent light is a laser taken from the group consisting of gas, liquid, crystal and semiconductor.

* * * * *